(12) United States Patent
Landon

(10) Patent No.: US 8,734,450 B2
(45) Date of Patent: May 27, 2014

(54) SAW BLADE

(75) Inventor: Ryan Lloyd Landon, Southaven, MS (US)

(73) Assignee: Smith & Nephew, Inc., Memphis, TX (US)

( * ) Notice: Subject to any disclaimer, the term of this patent is extended or adjusted under 35 U.S.C. 154(b) by 44 days.

(21) Appl. No.: 13/210,017

(22) Filed: Aug. 15, 2011

(65) Prior Publication Data

US 2012/0041443 A1   Feb. 16, 2012

Related U.S. Application Data

(60) Provisional application No. 61/373,522, filed on Aug. 13, 2010, provisional application No. 61/494,265, filed on Jun. 7, 2011.

(51) Int. Cl.
*A61B 17/16* (2006.01)

(52) U.S. Cl.
USPC ............... 606/82; 30/337; 30/339; 83/665; 83/698.11

(58) Field of Classification Search
USPC ............ 606/79, 82, 167, 169–171, 176–179, 606/86 R; 83/769, 589.597, 599, 782, 835, 83/665, 698.11, 776, 847, 848, 341; 30/340, 342–344, 330–339, 43.7, 43.8, 30/208–209, 166.3, 392, 355, 272.1, 30/272.4, 169, 348, 351, 166
See application file for complete search history.

(56) References Cited

U.S. PATENT DOCUMENTS

| | | | |
|---|---|---|---|
| 2,951,482 A * | 9/1960 | Sullivan | 606/176 |
| 3,905,374 A * | 9/1975 | Winter | 606/178 |
| 4,036,236 A * | 7/1977 | Rhodes, Jr. | 606/177 |
| 4,637,391 A | 1/1987 | Schlein | |
| 4,955,888 A | 9/1990 | Slocum | |
| 4,985,031 A | 1/1991 | Buss | |
| 5,178,626 A * | 1/1993 | Pappas | 606/178 |
| 5,306,285 A | 4/1994 | Miller | |
| 5,489,285 A * | 2/1996 | Goris | 606/82 |
| 5,554,165 A | 9/1996 | Raitt | |
| 5,643,270 A | 7/1997 | Combs | |
| 2004/0138668 A1 | 7/2004 | Fisher | |

(Continued)

FOREIGN PATENT DOCUMENTS

KR    578561 B1    5/2006

OTHER PUBLICATIONS

International Search Report for International Application No. PCT/US2012/047519, mailed Mar. 22, 2012.

(Continued)

*Primary Examiner* — Todd Manahan
*Assistant Examiner* — Marcela I Shirsat
(74) *Attorney, Agent, or Firm* — Fish & Richardson P.C.

(57) ABSTRACT

There is provided a surgical saw blade for use in orthopaedic surgery. The saw blade comprising: a mounting cavity having a first substantially triangular-shaped opening and a second substantially triangular-shaped opening in communication with, and inverted relative to, the first opening, the first and second opening collectively define two mounting slots that form an angle relative to one another. In some embodiments, the planar portion further comprises an offset planar shelf. The offset shelf may be oriented along the length of the planar portion to allow for longitudinal reciprocation or may be oriented across the width of the planar portion to allow for lateral reciprocation.

18 Claims, 22 Drawing Sheets

(56) References Cited

U.S. PATENT DOCUMENTS

| | | | |
|---|---|---|---|
| 2004/0221461 A1* | 11/2004 | Knisley et al. | 30/392 |
| 2005/0245935 A1* | 11/2005 | Casey et al. | 606/82 |
| 2009/0044679 A1* | 2/2009 | Souza et al. | 83/848 |
| 2009/0138017 A1 | 5/2009 | Carusillo | |

OTHER PUBLICATIONS

International Search Report for International Application No. PCT/US2011/047526, mailed Mar. 22, 2012.

* cited by examiner

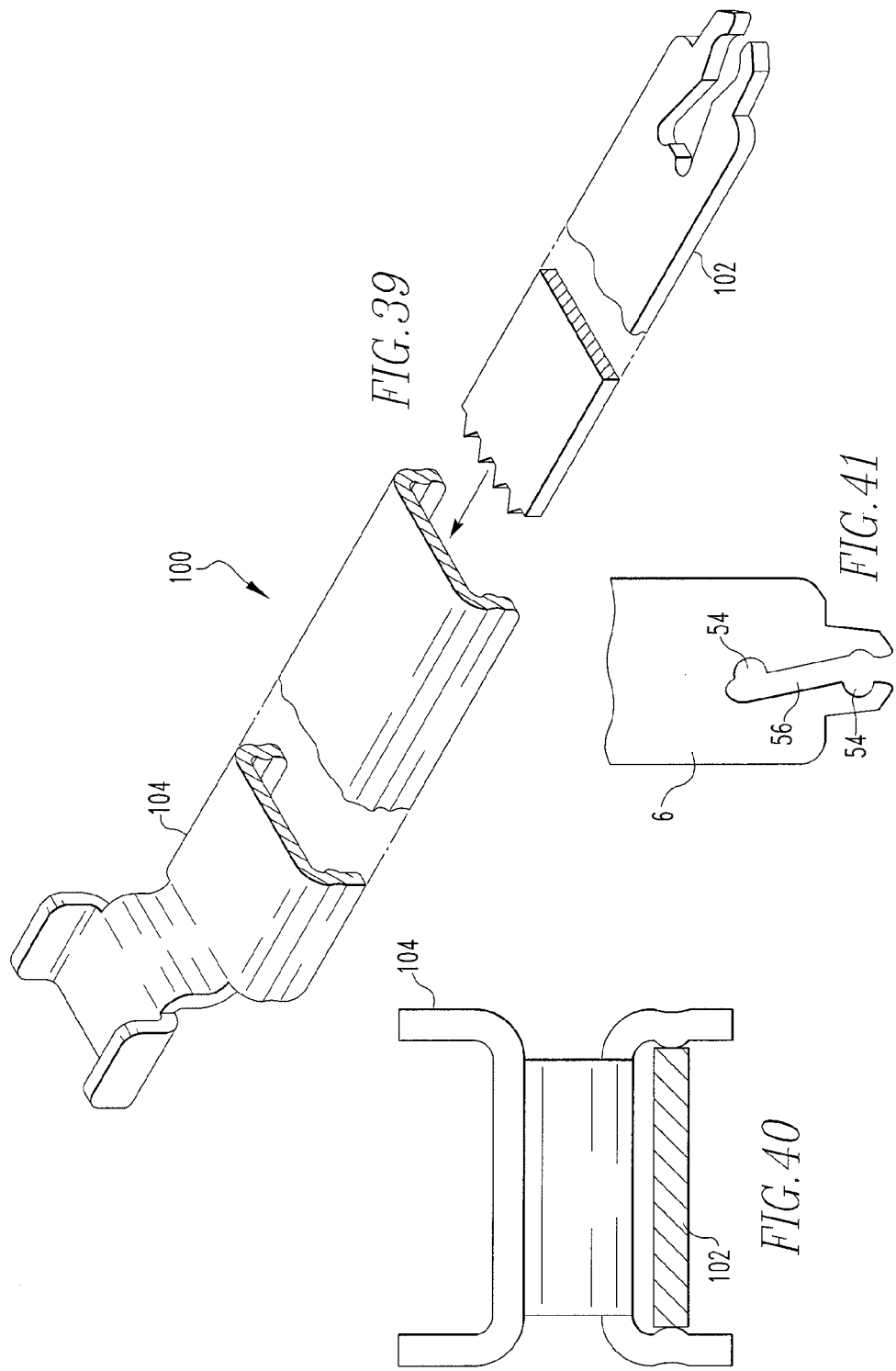

SAW BLADE

CROSS-REFERENCE TO RELATED APPLICATIONS

This application claims the benefit of U.S. Provisional Application No. 61/373,522, filed Aug. 13, 2010 and U.S. Provisional Application No. 61/494,265, filed Jun. 7, 2011. The disclosure of this prior application is incorporated by reference in its entirety.

BACKGROUND OF THE INVENTION

1. Field of the Invention

The present invention relates to saw hubs for use with powered surgical saws in orthopedic surgery and other operations involving cutting of bone.

2. Related Art

Powered saws are frequently used for surgical procedures including orthopedic surgery and other operations requiring cutting of bone. Such saws typically include a handpiece 2 by which the surgeon can support the saw 1, a hub 3 mounted on handpiece 2, and a saw blade 4 coupled to the hub 3, as seen generally in FIGS. 1-3. In use and upon activation by the surgeon, the hub moves to impart oscillatory motion to the saw blade rigidly attached to the hub. The integrity and security of the connection between the saw blade and the hub is of paramount importance for safe and effective operation of the saw. If the blade is not fully inserted and adequately secured within the hub, the repeated and rapid oscillations of the blade can lead to the disengagement of the blade during operation and thereby risk serious bodily injury. Further, an inadequately secured blade for an oscillating motion saw generates a significant amount of noise. This is because current saw blades do not tightly fit into the saw head slots.

Precise bone surgery requires a surgical saw and saw blade which can be threaded through surgical access incisions, fed down to tissue or bone requiring cutting or resection, and with the ability to make the cut or perform the resection without injuring or endangering the surrounding bone or tissue. Precise bone surgery also requires a surgical saw and saw blade which can be utilized for deep cuts while maintaining minimal, atraumatic motion of the longitudinal sides of the saw blade, and transverse motion of the toothed end of saw blade, allowing effective cutting and or resection of tissue or bone.

SUMMARY OF THE INVENTION

At least some of the embodiments described herein address some of the aforementioned problems by providing a saw blade designed for improved connection of the blade to the hub of a saw. There is provided a surgical saw blade for use in orthopaedic surgery. The saw blade comprising: a mounting cavity having a first substantially triangular-shaped opening and a second substantially triangular-shaped opening in communication with, and inverted relative to, the first opening, the first and second opening collectively define two mounting slots that form an angle relative to one another. In one embodiment, the first opening and the second opening have rounded corners. In another embodiment, the first opening includes side walls and a distally-located base wall having ears separated by a depth-stop connecting wall. In yet another embodiment, the connecting wall is straight, concave, or convex. In some embodiments, the saw blade further comprises a mounting portion and a planar portion extending longitudinally from the mounting portion, and the mounting cavity is located on the mounting portion. In still another embodiment, the planar portion further comprises an offset planar shelf. In one embodiment, the offset shelf is oriented along the length of the planar portion to allow for longitudinal reciprocation. In another embodiment, the offset shelf is oriented across the width of the planar portion to allow for lateral reciprocation. In yet another embodiment, the planar portion further comprises teeth. In still another embodiment, the teeth are arranged in a linear or arcuate fashion. In one embodiment, the teeth are oriented along the length of the planar portion to allow for longitudinal reciprocation. In still another embodiment, the teeth are oriented across the width of the planar portion to allow for lateral reciprocation.

Embodiments disclosed herein provide a saw blade having a mounting cavity for mounting the saw blade on the hub of a saw. In one embodiment, the mounting cavity is formed of a first substantially triangular-shaped opening and a second substantially triangular-shaped opening in communication with, and inverted relative to, the first opening that collectively define two mounting slots that form an angle relative to one another.

Embodiments disclosed herein also include provision of a blade locking mechanism having a mounting arm and at least two locking pins provided in the cam. In use, the locking pins are retracted and the saw blade is inserted into a slot in the cam so that the mounting arm is received in the mounting cavity. The locking pins are then released and spring upwardly to engage one of the mounting slots, gradually biasing the mounting arm into the other of the mounting slots until the locking pins can fully extend into their respective positions within the mounting slot. The locking pins thereby retain the mounting arm in one of the mounting slots via their engagement with the other of the mounting slots and in this way prevent the blade from backing out of the cam.

The embodiments disclosed herein create and retain a rigid, secure connection between the saw blade and hub even after repeated and rapid oscillations of the saw blade during use. Moreover, the disclosed connection configuration renders it easy to mount and dismount the saw blade from the hub quickly without the need for tools, such as a wrench or key. Thus, embodiments disclosed herein eliminate the need to provide and sterilize such tools in the surgical suite and account for their presence after surgery. Rather, the embodiments disclosed herein make replacing saw blades, which often occurs during surgery, a relatively simple task and thus enhances the versatility of the saw.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIGS. 35-39 illustrate additional embodiments of a saw blade.

FIG. 40 illustrates an end view of the saw blade shown in FIG. 39.

FIG. 41 illustrates another embodiment of the saw blade.

DETAILED DESCRIPTION OF THE EMBODIMENTS

The following description of the preferred embodiment(s) is merely exemplary in nature and is in no way intended to limit the invention, its application, or uses.

Figure 1:
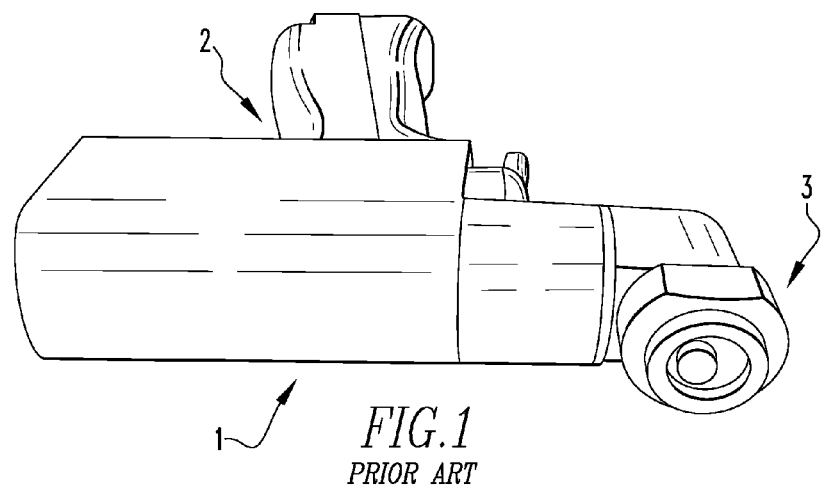
FIG. 1 is a schematic illustration of a prior art saw including a handpiece with a hub.
Figure 2:
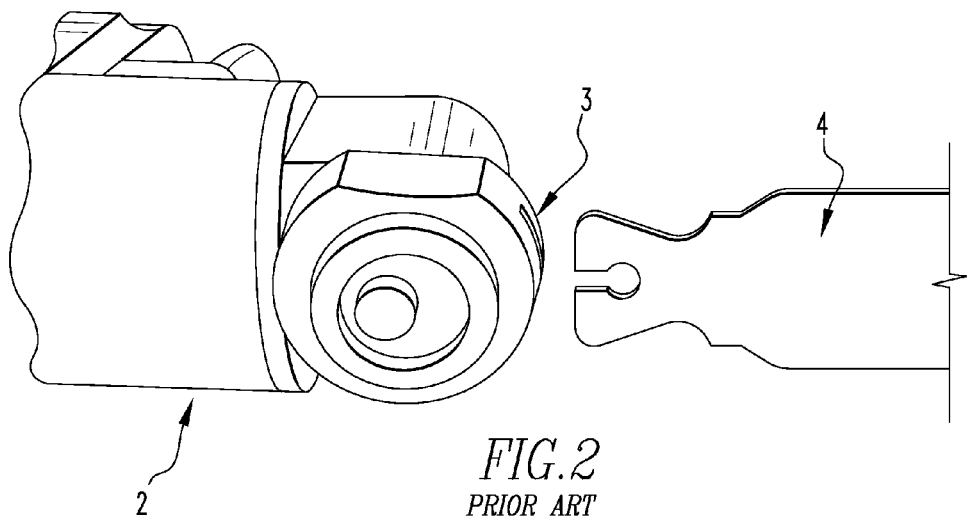
FIG. 2 is a schematic illustration of a prior art saw blade positioned adjacent the saw of FIG. 1.
Figure 3:
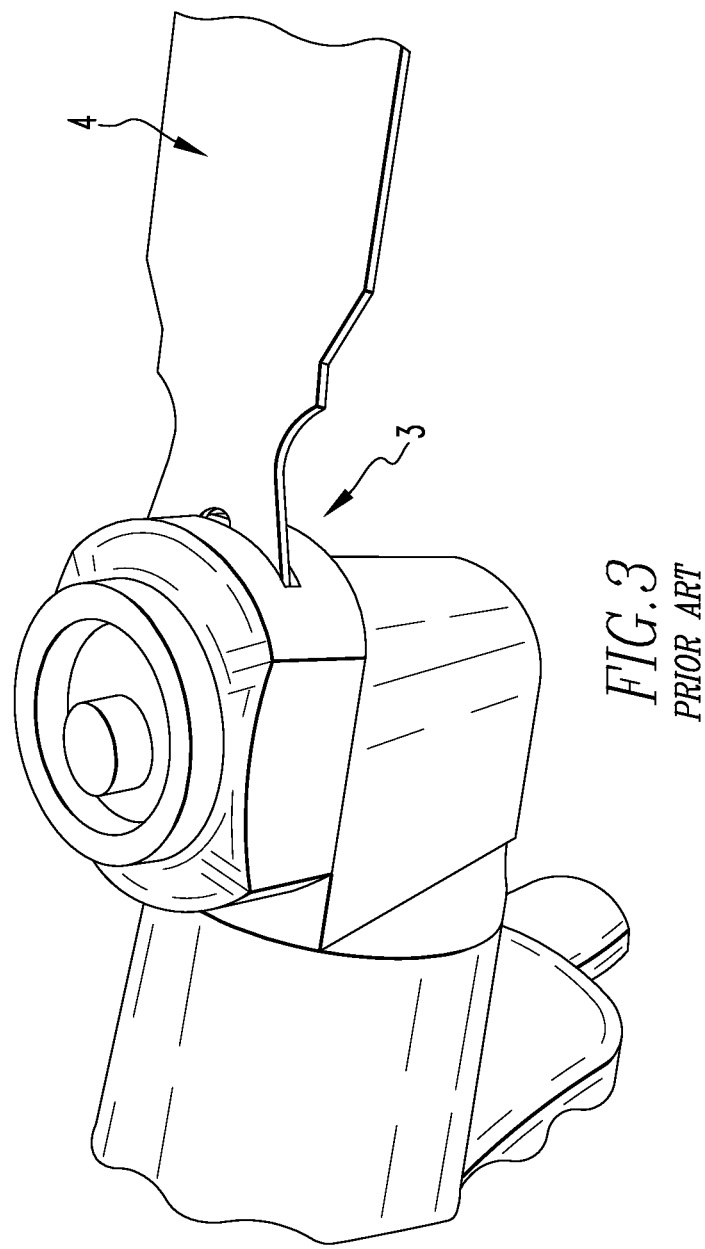
FIG. 3 is a schematic illustration of the saw blade of FIG. 2 inserted into a slot in the hub of the saw of FIG. 1.
Figure 4:
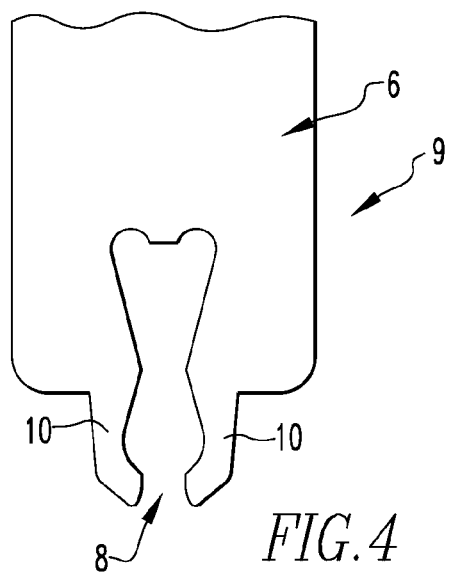
FIG. 4 is a partial top plan view of one embodiment of a saw blade.
Figure 18A:
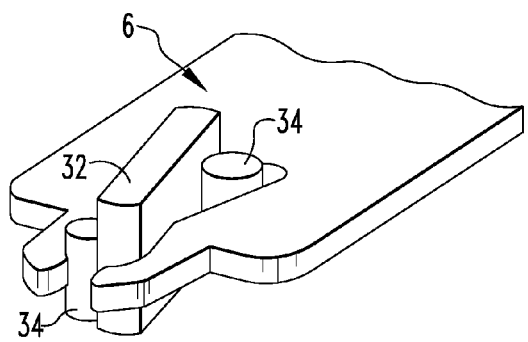
Figure 18B:
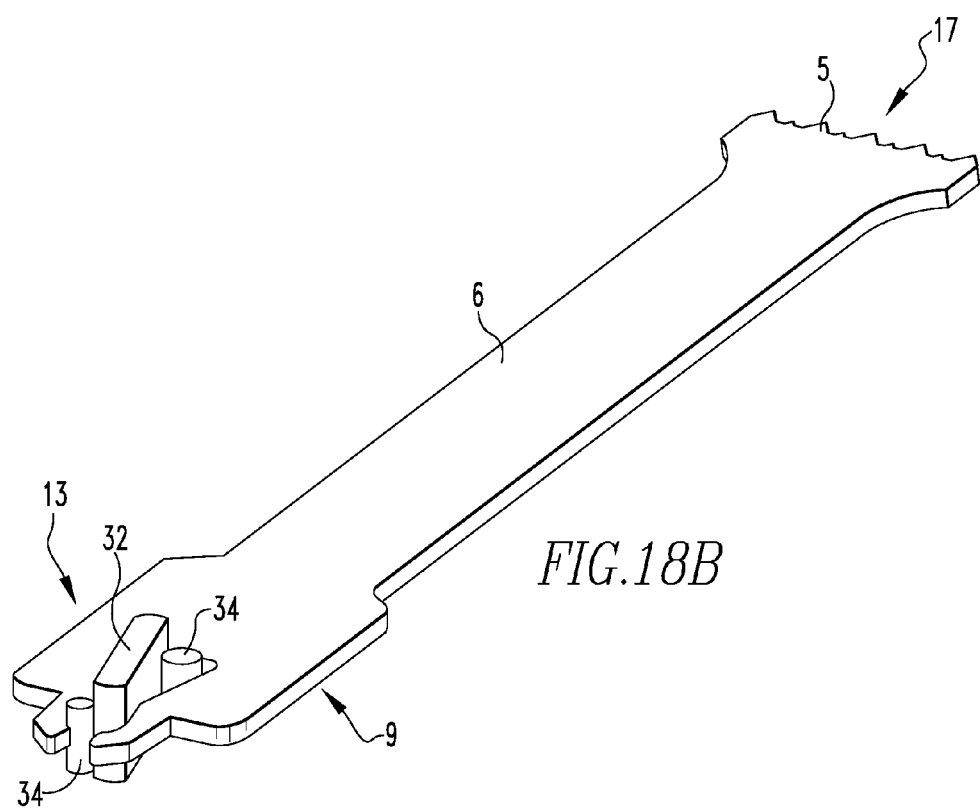
Figure 19:
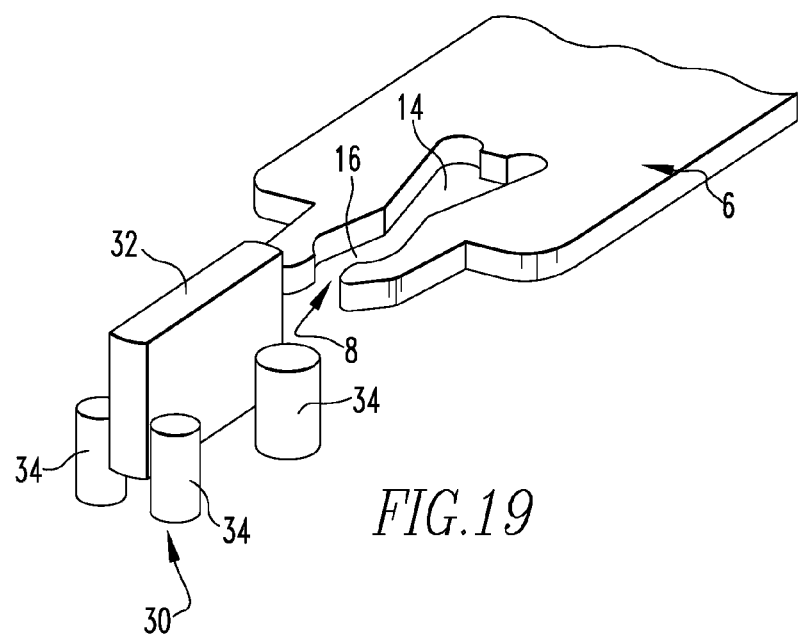
FIGS. 19-27 schematically depict the saw blade of FIG. 4 being mounted on a second type of blade locking mechanism provided in the hub of a saw.
Figure 20:
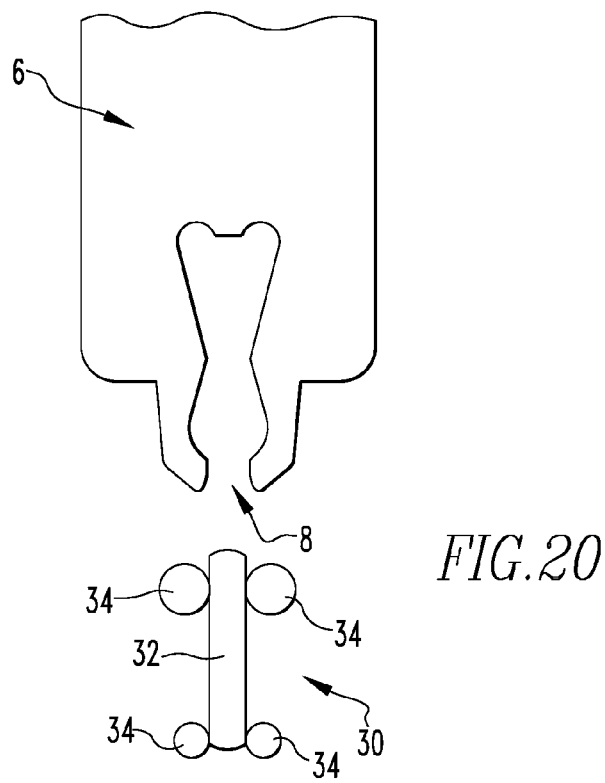
Figure 21:
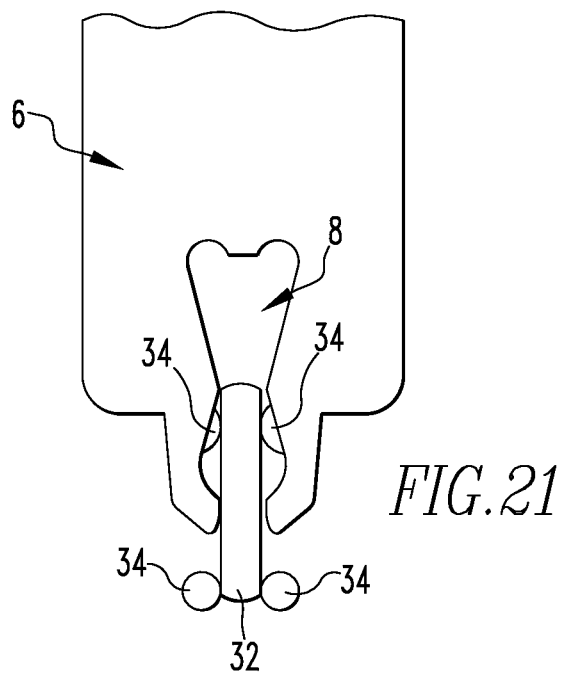
Figure 22:
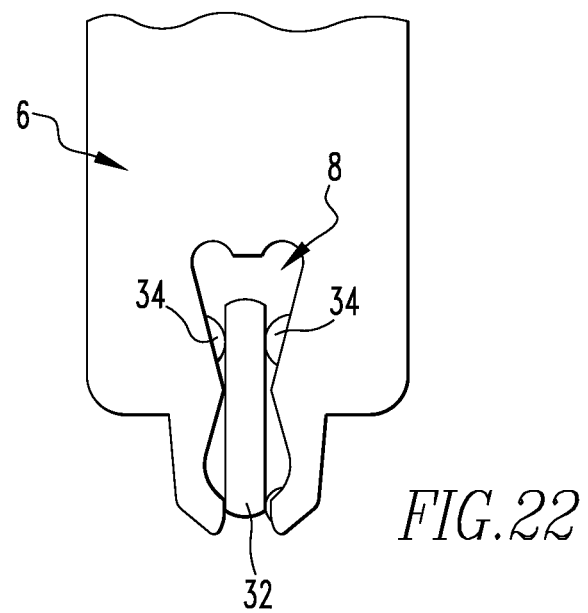
Figure 23:
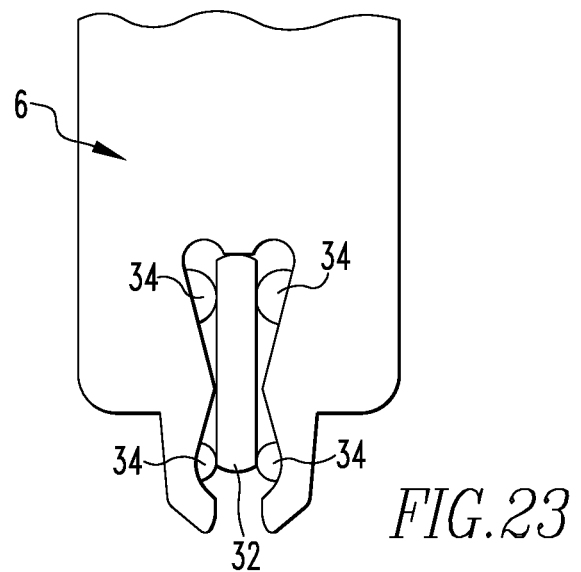
Figure 24A:
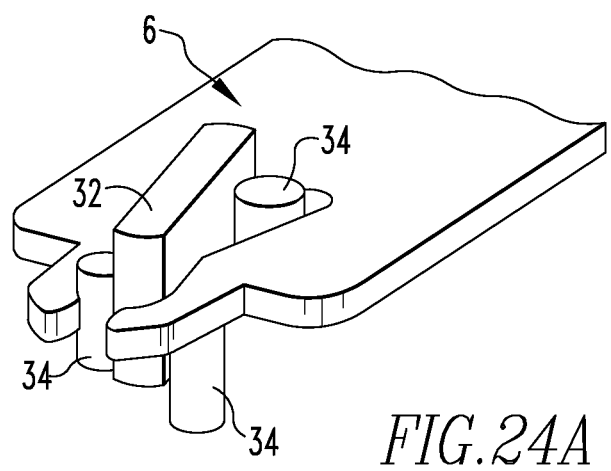
Figure 24B:
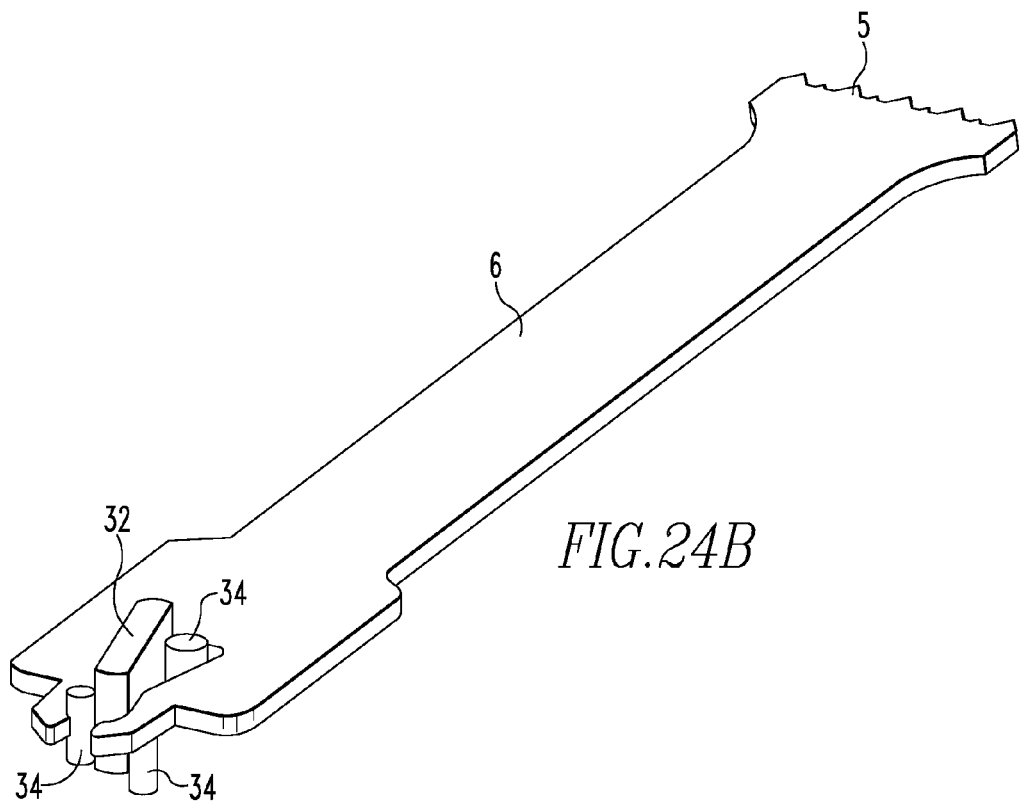
Figure 25A:
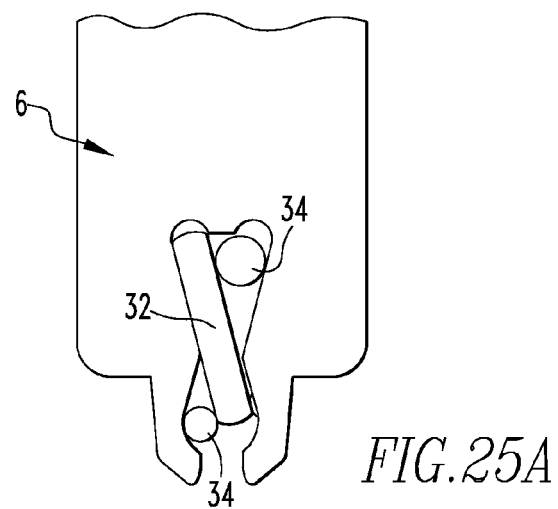
Figure 25B:
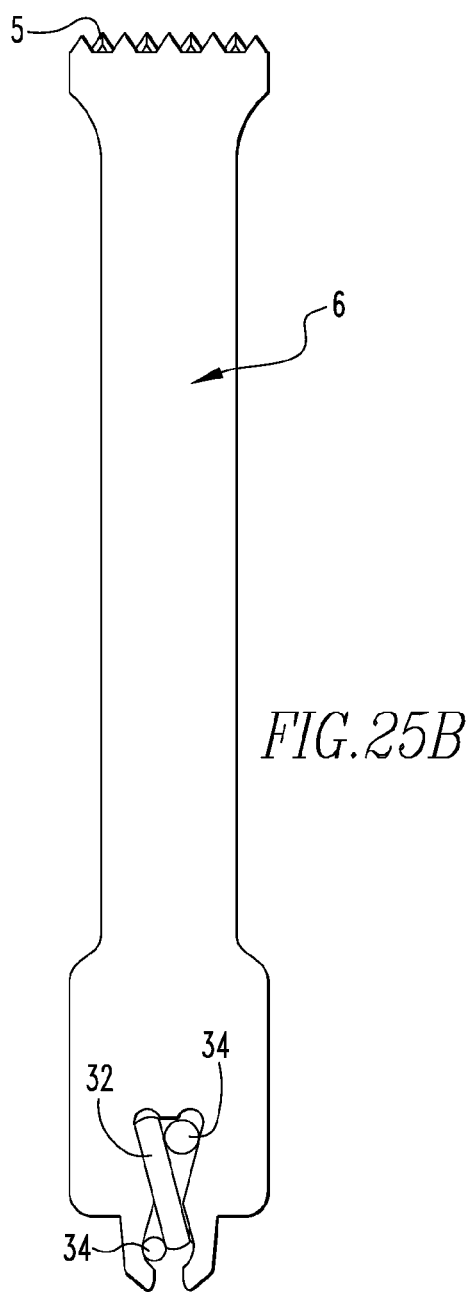
Figure 26:
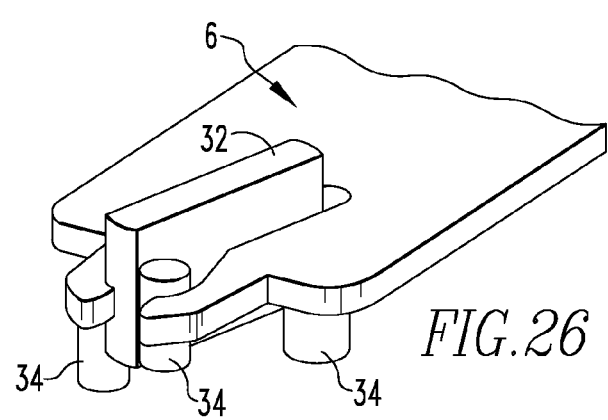
Figure 27:
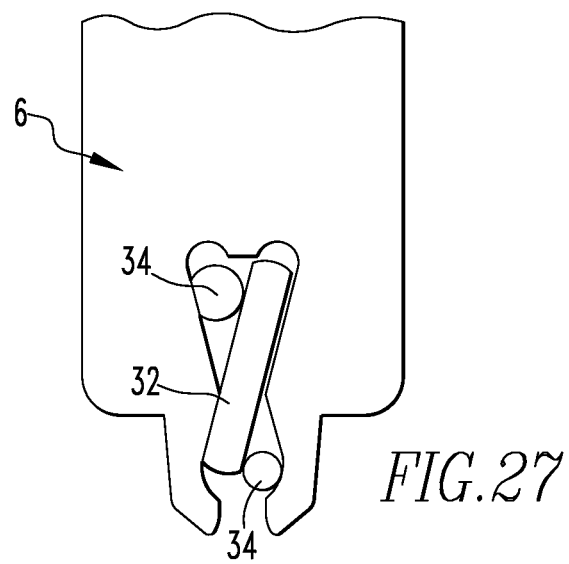

FIG. 4 illustrates one embodiment of a saw blade 6. The saw blade 6 may be formed from any material having suitable structural integrity and strength to cut bone. Suitable materials include, but are not limited to, metallic materials, such as stainless steel. One of skill in the art will readily understand that teeth 5 or other means for cutting bone would be provided on the saw blade. (See, e.g., FIGS. 18B, 24B, and 25B). Such teeth 5 could be provided along a distal end or side edge(s) of the saw blade 6. Teeth 5 may be arranged in a linear or in an arcuate fashion. The saw blade 6 also includes a mounting portion 9.

Figure 28:
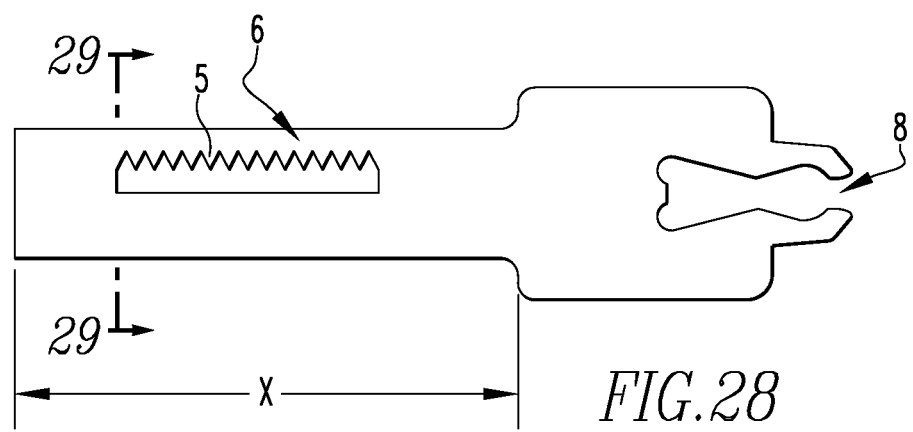
FIG. 28 is a top plan view of another embodiment of the saw blade.

Teeth 5 need not be positioned along an outermost edge of saw blade 6, nor must saw blade 6 be planar. Rather, as illustrated in FIGS. 28-32, teeth 5 may be positioned at any location within saw blade 6, and saw blade 6 may be configured (e.g., bent) so that teeth 5 are exposed for cutting. In FIG. 28, teeth 5 are oriented within saw blade 6 along its length and reciprocate longitudinally (i.e., in direction x). In another embodiment, teeth 5 can be oriented within saw blade 6 across its width and reciprocate laterally (i.e., in direction y) as shown in FIG. 32. However, teeth 5 may be provided in blade 6 at any location and blade 6 can be configured in any way to ensure exposure of teeth 5 for cutting.

Figure 29:
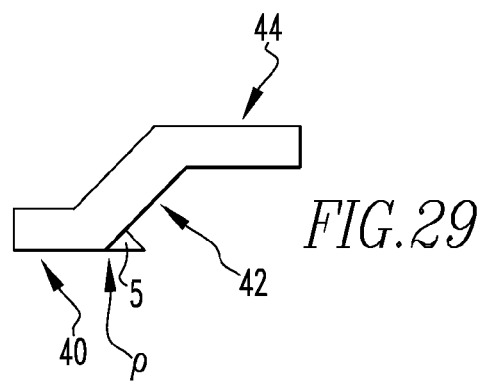
FIG. 29 is a cross sectional view of the saw blade of FIG. 28 taken along line 29-29.
Figure 31:
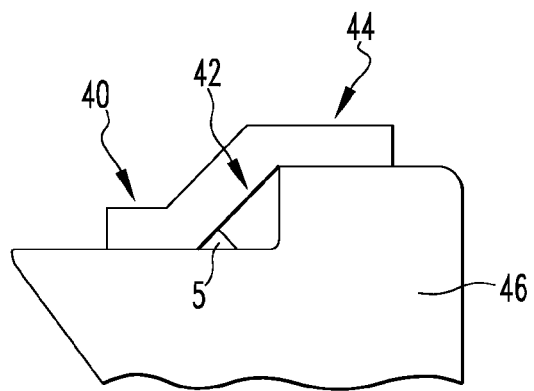
FIG. 31 is a schematic cross sectional view of the saw blade of FIG. 28 positioned on a bone.
Figure 32:
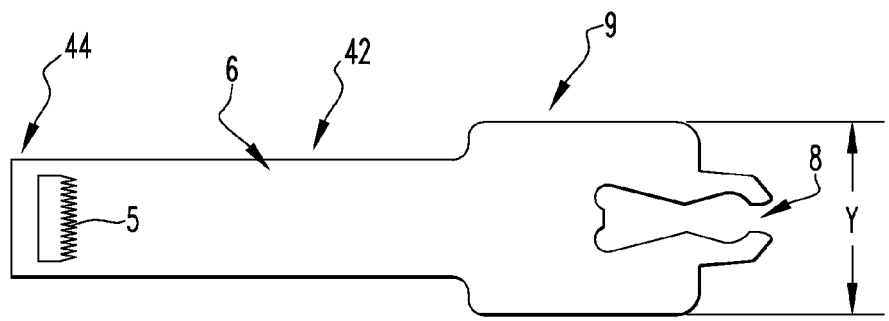
FIG. 32 is a top plan view of another embodiment of a saw blade.

As shown in FIG. 29, blade 6 may be, but does not have to be, shaped to have a first planar portion 40, the underside of which is designed to contact bone 46 to properly orient blade 6 for cutting on bone 46 (see FIG. 31). First planar portion 40 transitions in a transition portion 42 to a second offset shelf portion 44. In some embodiments, transition portion 42 bends or otherwise extends upwardly from first portion 40 at a transition point P. By virtue of this upward extension, teeth 5, which extend from first portion 40, are exposed so that when blade 6 is placed on bone 46, teeth 5 are able to engage and cut bone 46. Second portion 44 extends from the transition portion 42 and is also designed to rest on bone 46 (see FIG. 31) to keep the blade 6 level and thus prevent the blade 6 from moving downwardly. In this way, second portion 42 guides the blade and helps ensure that teeth 5 do not cut too deeply into bone 46 but rather that bone 46 is cut at a consistent depth. One of skill in the art will understand that the first portion 40, transition portion 42, and second portion 44 may be oriented at any angle relative to each other depending on the desired cut and each may be of any thickness and need not be the same thickness along the blade. One of skill in the art will also understand that the embodiment of the blade shown in FIG. 32 is structurally similar to that of FIG. 28 but with the blade rotated 90° and thus would have a cross-sectional shape similar to that shown in FIG. 29 if the cross-section were taken along the length of the blade (as opposed to across the width of the blade as in FIG. 29). In some embodiments, second portion 44 includes a chamfer or rounded edge to reduce the chance of its tip from catching or snagging on bone. One of skill in the art would understand that there are a variety of techniques and methods for manufacturing the blades, including, but not limited to, bending or welding. All such techniques and methods are contemplated herein. In the embodiment depicted in FIG. 32, the saw blade 6 includes the mounting portion 9, the mounting cavity 8, the planar portion 42, and the offset shelf portion 44.

Figure 30:
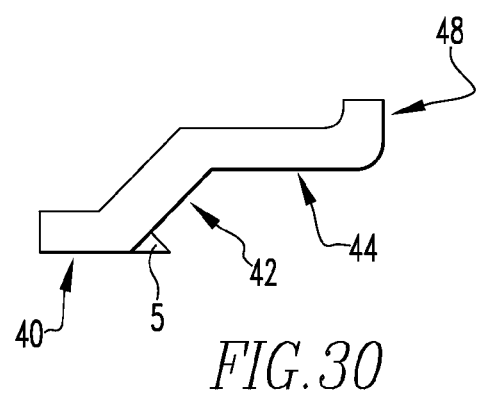
FIG. 30 is a cross sectional view of another embodiment of a saw blade.

In an alternative embodiment shown in FIG. 30, second portion 44 includes an upstanding rib 48 that imparts stiffness to blade 6. The stiffness imparted to blade 6 by rib 48 also assists in repeatability of the cut at a consistent depth. The rounded corner provided by the upstanding rib 48 conveniently provides a surface that is less prone to catching or snagging on the surface of the bone 46. Again, however, blade 6 can be of any cross-sectional shape and is not limited to the embodiments disclosed herein. Moreover, embodiments of blades 5 disclosed herein may be provided with a mounting cavity 8 and connected to a saw hub as disclosed below or can be connected to a saw hub in other ways.

In some embodiments, second portion 44 may be offset from first portion 40 in discrete amounts. For example, second portion 44 may be offset from the first portion by 2 mm. The particular offset may range from between 0.5 mm to 10 mm and more particularly from about 1 mm to about 4 mm. In some embodiments, there may be provided a series of saw blades, each with a particular offset. For example, there may be provided a series of saw blades ranging from 1 to 6 mm in 1 mm increments. In this manner, a surgeon could select a saw blade with a desired offset to cut off a selected amount or thickness of bone.

Figure 33:
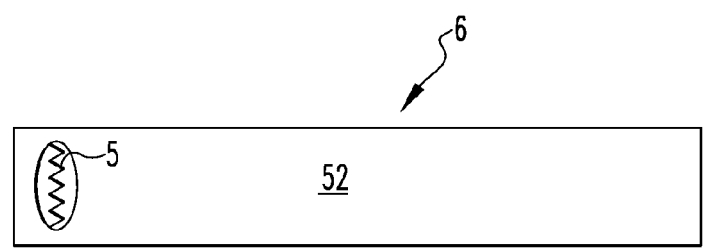
FIG. 33 is a top plan view of yet another embodiment of a saw blade.
Figure 34:
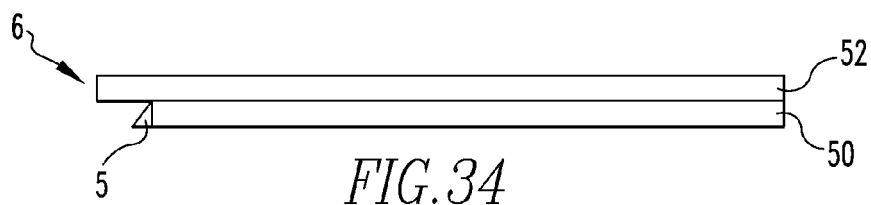
FIG. 34 is a side elevation view of the saw blade of FIG. 33.

In an alternative embodiment of blade 6, the blade 6 does not include a transition portion 42. Rather, the blade 6 is formed by attaching or otherwise forming two plates 50, 52 together, as shown in FIGS. 33 and 34. Teeth 5 are provided on plate 50 to cut bone. Plate 52 can extend beyond the teeth 5 and rest on bone to guide the blade 6 and ensure that the blade 6 remains level during cutting.

Figure 35:
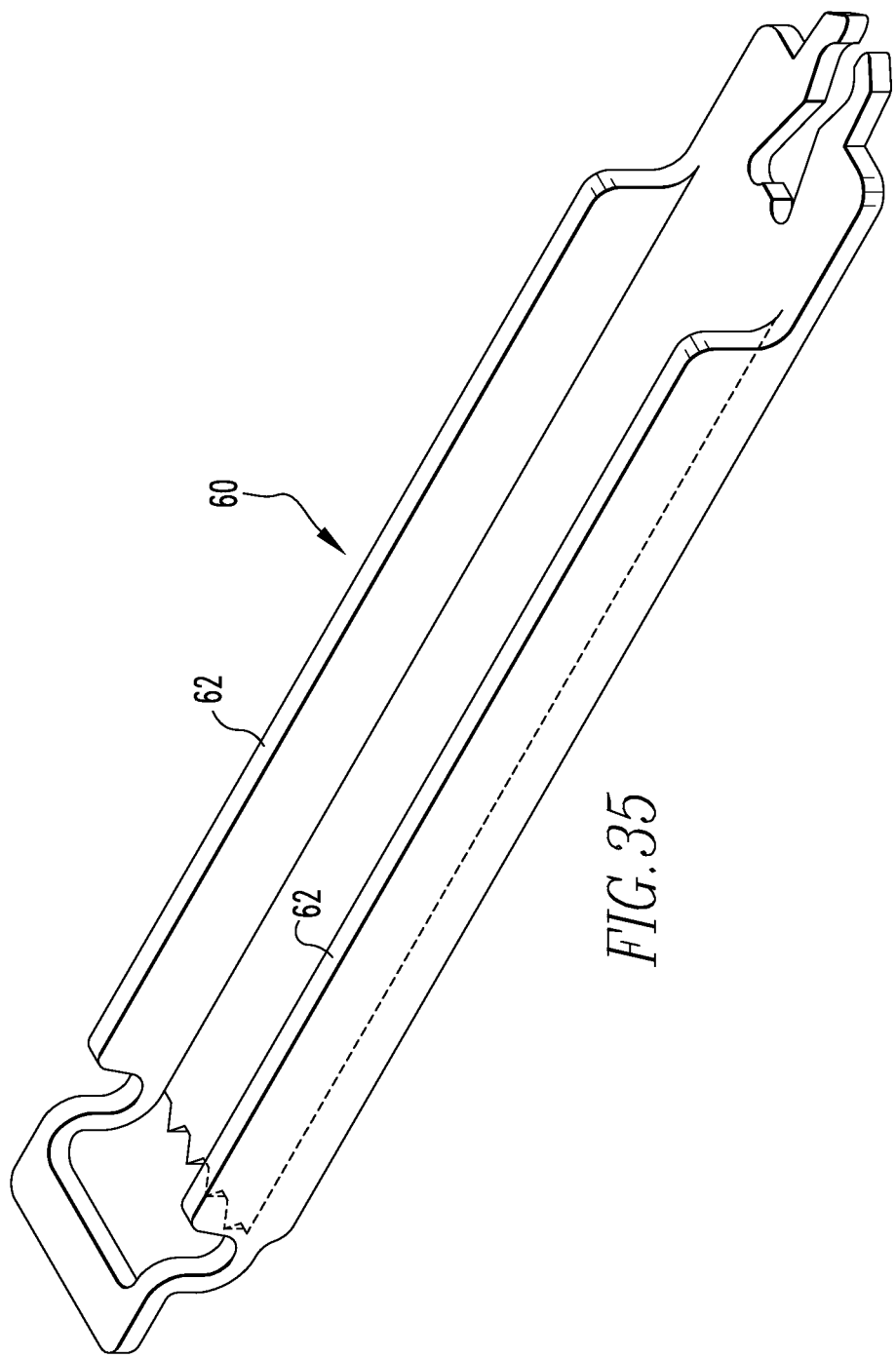
Figure 36:
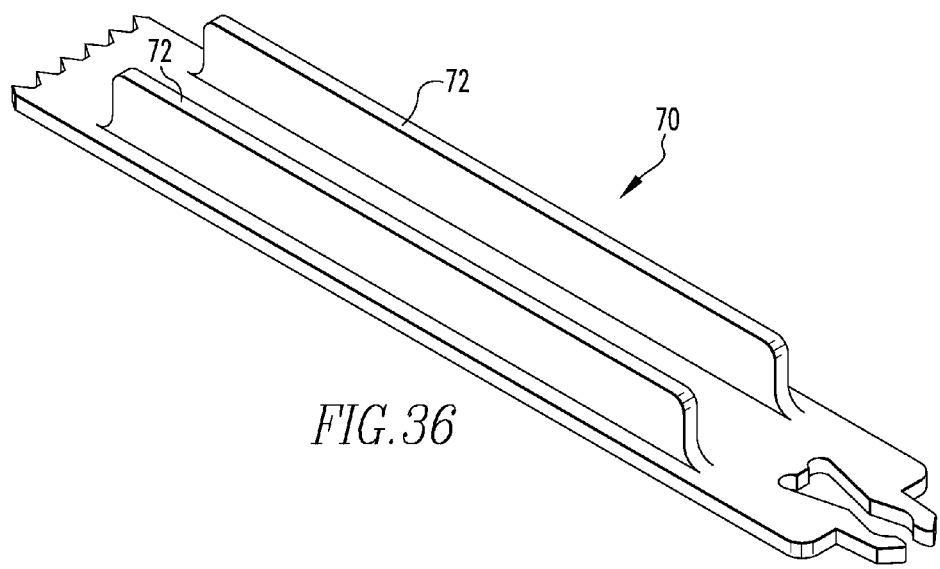
Figure 37:
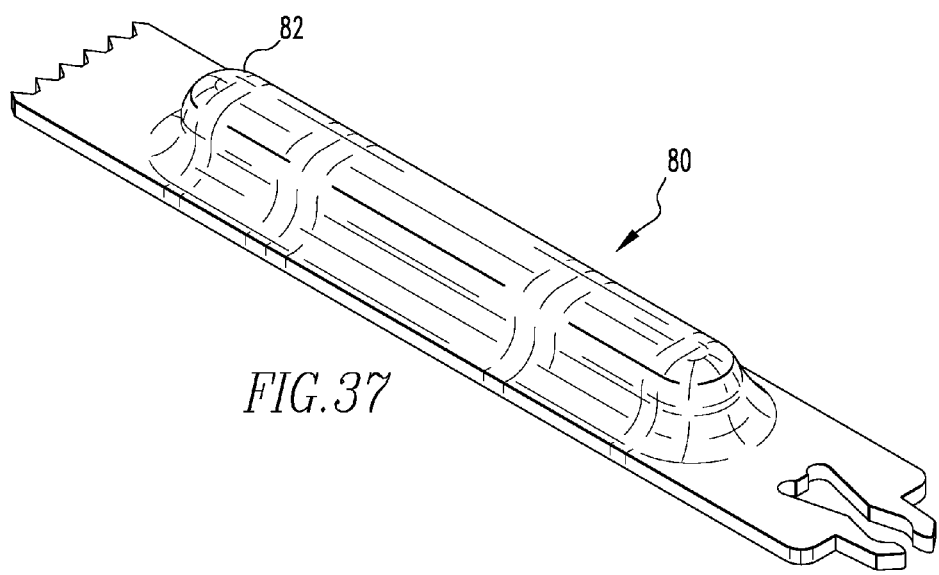
Figure 38:
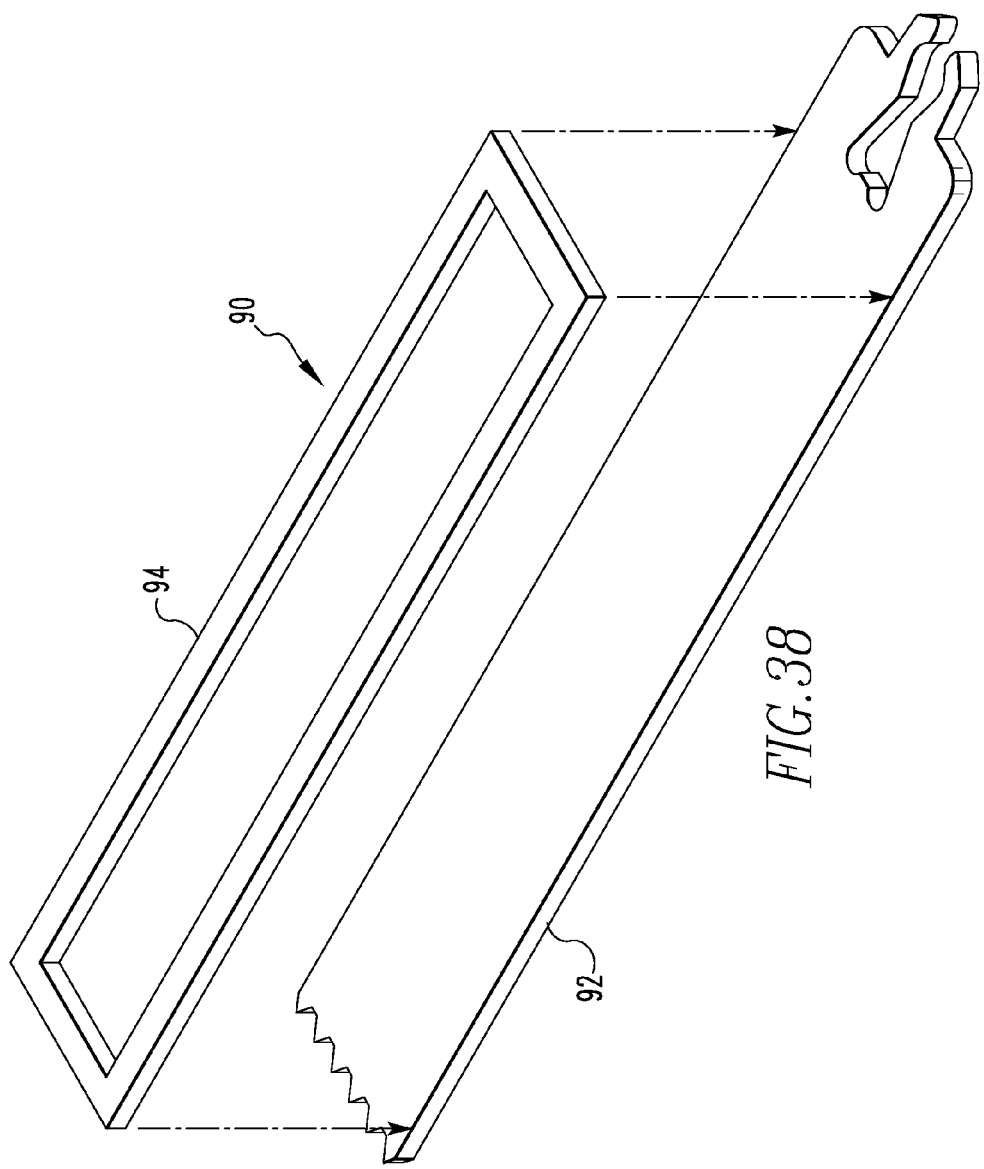

Reinforcing features may be provided on, or coupled to, the blade 6 to impart stiffness and structural integrity to the blade, as generally shown in FIG. 35. By way only of example, wings (FIG. 35), fins or ribs (FIG. 36), and/or arches (FIG. 37) may be provided along the length or width of the blade and may be formed integrally with the blade or formed separately and subsequently attached (such as via welding or any other mechanical or chemical retention means) to the blade. If formed separately from the blade, the reinforcing features can, but need not, be made from the same material as the blade.

In some embodiments (see generally 38), the saw blade 92 is coupled to a reinforcing component 94 that imparts stiffness and structural integrity to a saw blade assembly 90. The reinforcing component 94 may be configured for mounting on or receiving and retaining the blade 92, such as via a snap-fit or snap-on connection or any other connection means. Alternatively, the reinforcing component 94 may be fastened or welded to the saw blade 92. Again, the reinforcing component can, but need not, be made from the same material as the blade.

In the embodiment shown in FIGS. 39 and 40, a guide 104 attaches to a saw blade 102 to form a saw blade assembly 100. The guide 104 may be configured for mounting on or receiving and retaining the blade 102. For example, a snap-fit or snap-on connection may be provided between the guide 104 and the blade 102. Alternatively, the guide 104 may be fastened or welded to the saw blade 102. The guide 104 includes a connection channel to receive the saw blade 102 and a ledge portion 104. The ledge portion is designed to rest on bone to keep the blade 102 level and thus prevent the blade 102 from moving downwardly. In this way, the guide 104 guides the blade and helps ensure that teeth do not cut too deeply into bone but rather that bone is cut at a consistent depth. In some embodiments, the ledge portion is offset from the connection channel in discrete amounts. For example, the ledge portion may be offset from the connection channel by 2 mm. The particular offset may range from between 0.5 mm to 10 mm and more particularly from about 1 mm to about 4 mm. In some embodiments, there may be provided a series of guides 104, each with a particular offset. For example, there may be provided a series of guides 104 ranging from 1 to 6 mm in 1 mm increments. In this manner, a surgeon could select a guide with a desired offset to cut off a selected amount or thickness of bone. The guide 104 may connect or be used in conjunction with saw blades disclosed herein or saw blades of the prior art.

Referring once again to FIG. 4, the saw blade 6 includes a mounting portion with a mounting cavity 8. The mounting cavity is defined between extension arms 10 located on the end of the saw blade 6 intended for mounting on the hub of a saw. The mounting cavity 8 may extend distally any distance into the saw blade 6 provided that the integrity and operation of the saw blade 6 is not detrimentally impacted.

Figure 5:
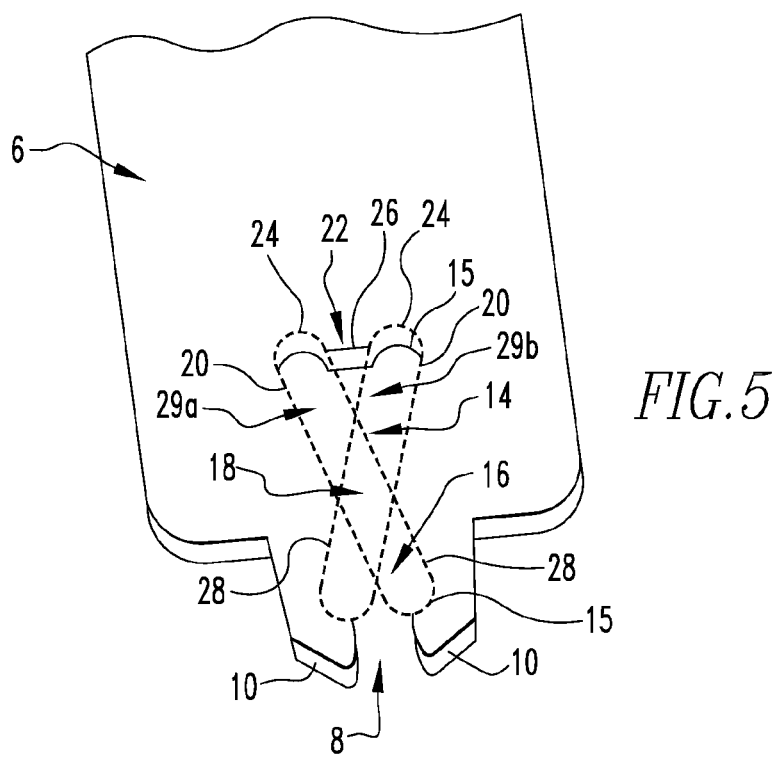
FIG. 5 is a partial top perspective view of the saw blade of FIG. 4.

While the mounting cavity 8 may be a variety of different shapes, in the embodiment of FIG. 5, the mounting cavity 8 is formed with two mounting slots 29a, 29b (shown in broken lines in FIG. 5) that extend along the length of the blade 6 at an angle to each other and to the longitudinal axis of the blade 6. In the embodiment shown in FIG. 5, slots 29a, 29b are mirror-images of each other, but need not be. While a variety of different geometries are contemplated, in some embodiments the mounting slots 29a, 29b form at an angle of about 20 degrees to about 40 degrees relative to one another. In other embodiments, the mounting slots 29a, 29b form at an angle of about 30 degrees relative to one another. It may be desirable, but certainly not necessary, to provide a symmetrical mounting cavity 8 (as is shown in FIG. 5) so that the saw blade 6 can then be mounted onto the saw hub with either side up. Those of ordinary skill in the art would understand that one of the mounting slots 29a, 29b is intact and capable of load-bearing, and the other mounting slot serves as a set of opposable surfaces to secure the blade during oscillatory motion. Further, one of ordinary skill in the art would understand that the angle between the mounting slots 29a, 29b may be designed and constructed to cause a tip or middle of a mounting pin to engage first depending upon whether the primary concern is tool wear or noise.

Figure 6:
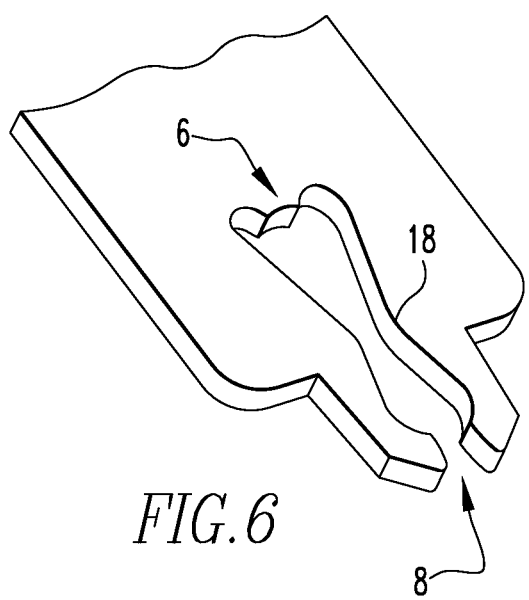
FIG. 6 is a partial top perspective view of another embodiment of a saw blade.

In one embodiment, the diagonal mounting slots 29a, 29b cross to form a first generally triangular-shaped opening ("first opening 14") and a second generally triangular-shaped opening ("second opening 16") in communication with, and inverted relative to, the first opening 14. Alternatively, the first opening 14 and the second opening 16 could be characterized as V-shaped and appear generally as opposing ">" and "<" symbols. In some embodiments and as shown in the Figures, the first opening 14 and the second opening 16 have rounded corners 15. While the intersection 18 of the first opening 14 and the second opening 16 is shown in FIG. 5 as substantially pointed, it need not be. Rather, as shown in FIG. 6, the intersection 18 may be more rounded. The first opening 14 includes side walls 20 and a distally-located base wall 22 having ears 24 separated by a connecting wall 26. The connecting wall 26 may serve as a depth-stop. The connecting wall 26 may be straight, concave, or convex and in some embodiments is concave in that it slightly extends in the direction of ears 24. The second opening 16 is defined by side walls 28. Each mounting slot 29a, 29b extends diagonally between an ear 24 of first opening 14 and a corner 15 of second opening 16.

Figure 7:
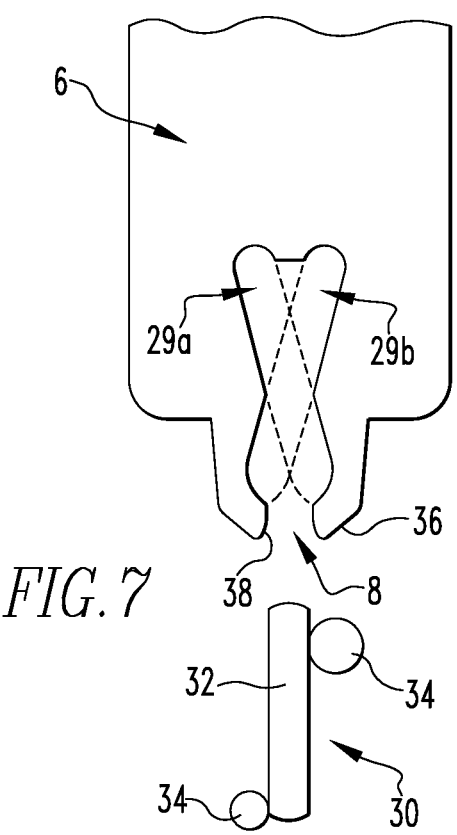
FIGS. 7-18B schematically depict the saw blade of FIG. 4 being mounted on a first type of blade locking mechanism provided in the hub of a saw.
Figure 8:
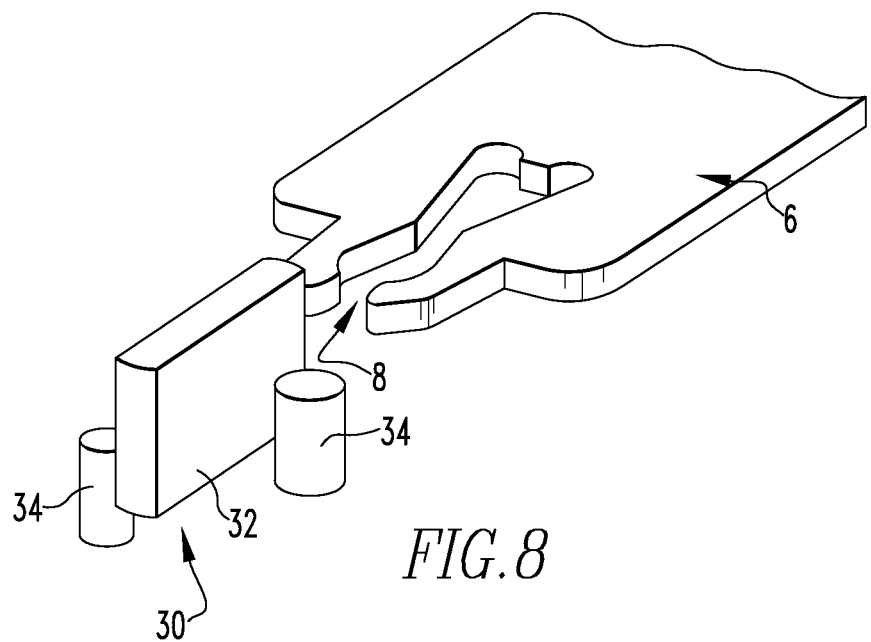
Figure 9:
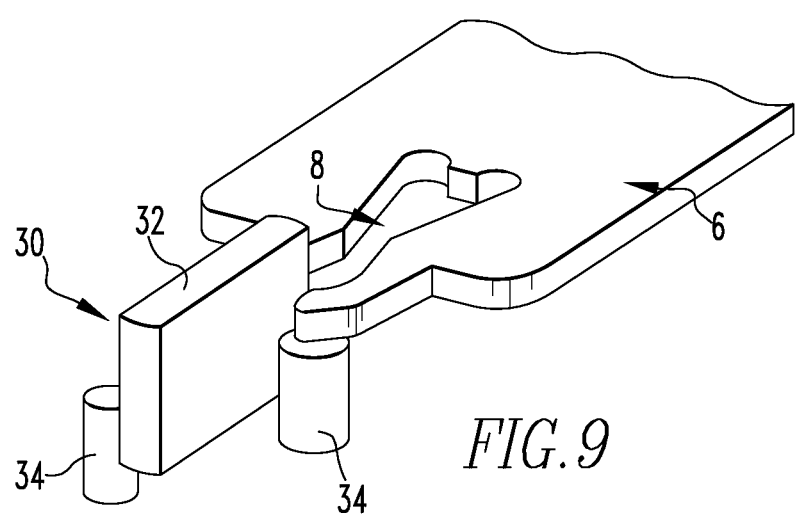
Figure 10:
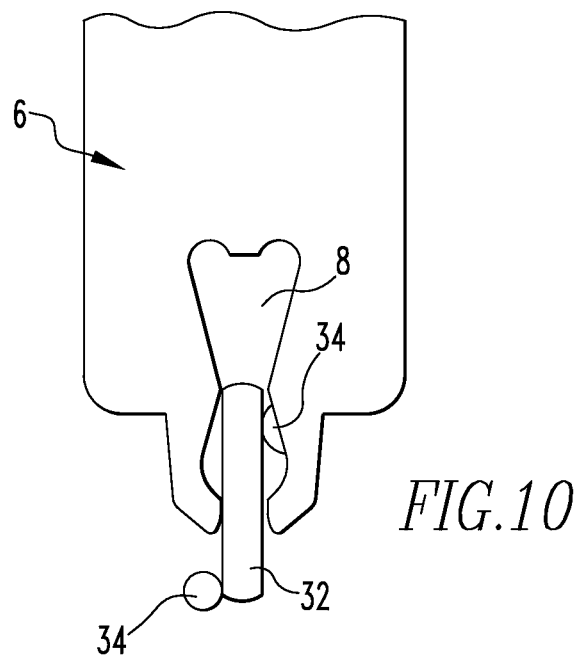
Figure 11:
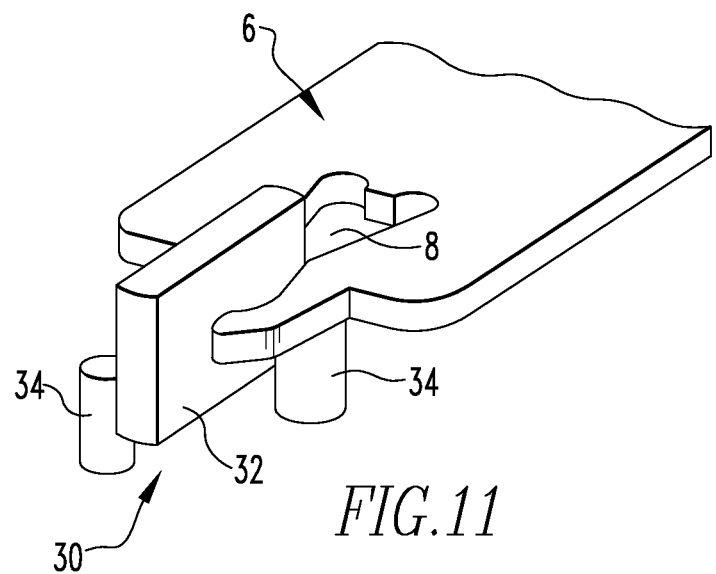
Figure 12:
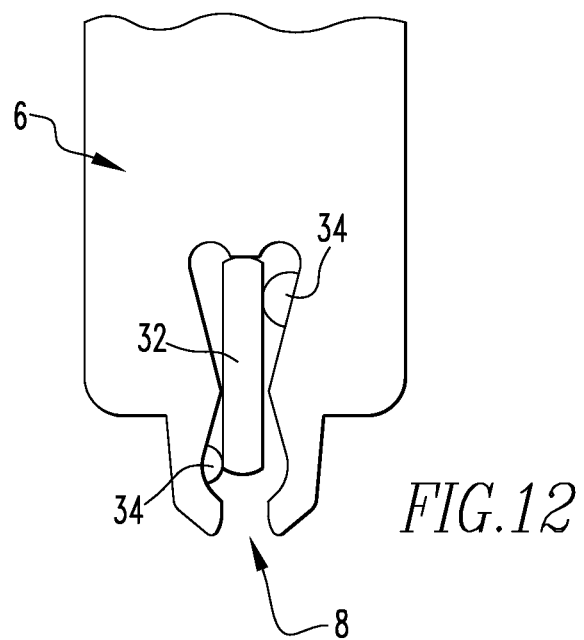
Figure 13:
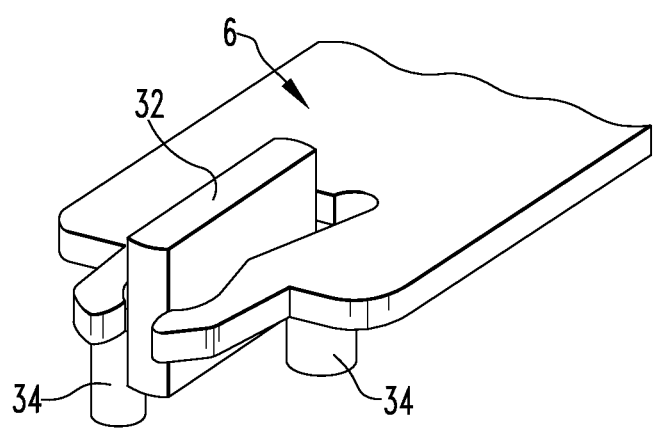
Figure 14:
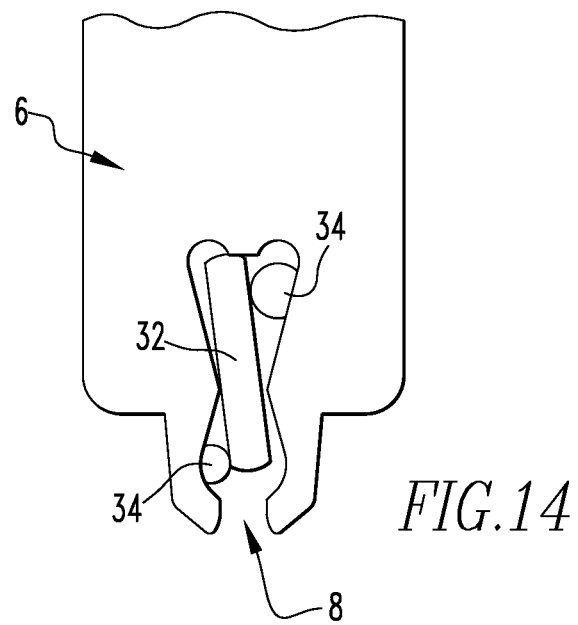
Figure 15:
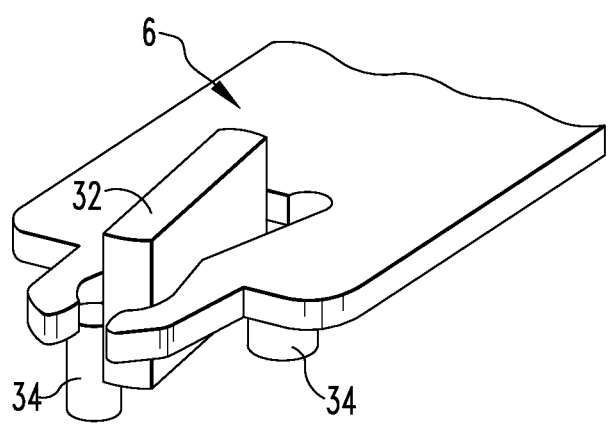
Figure 16:
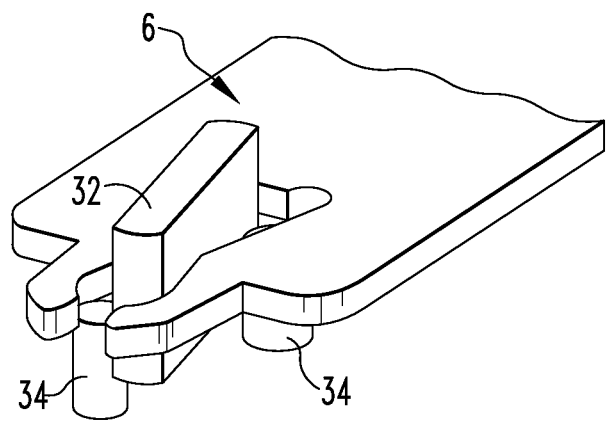
Figure 17:
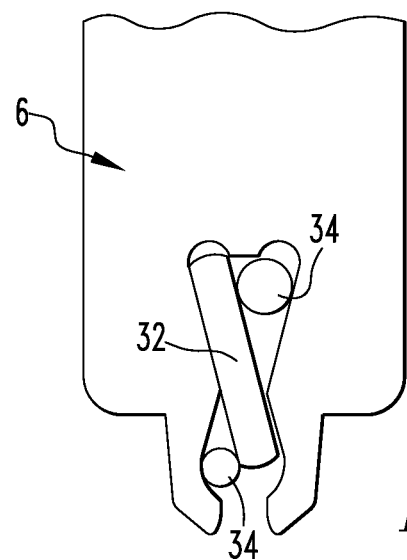

In use, saw blade 6 is attached to the hub of a saw via the mounting cavity 8. A blade locking mechanism 30 is provided in the hub to engage the saw blade 6. In one embodiment, the blade locking mechanism 30 includes an mounting arm 32 and locking pins 34 (shown schematically in FIG. 7) provided within the hub (not shown). In some embodiments, the locking pins 34 are provided on opposite sides and opposite ends of the mounting arm 32. In other embodiments, the locking pins 34 are provided on the same side and/or the same end. If the locking pins 34 are provided on the same side, then only one of the locking pins engages depending upon the direction the blade is rotated to lock it in place. If the locking pins 34 are located on the same end, then only one pin engages and engages always on the same end. In the case where the locking pins 34 are located on the same end and only one of which is engaged, there is provided a mechanism to allow the pins to expand into the space otherwise the blade could be loose and rattle in a longitudinal direction. An actuator (not shown) is provided on the handpiece and is connected to, and thus controls positioning of, locking pins 34 within the hub. More specifically, upon actuation of the actuator, the locking pins 34 are depressed relative to the mounting arm 32. In some embodiments, the locking pins 34 are spring-loaded. In some embodiments, the blade locking mechanism 30 includes only a single pin 34. In the depicted embodiment, locking pins 34 are illustrated as round but those having ordinary skill in the art would understand the pins could be any shape, such as square, rectangular, triangular, octagonal, C-shaped, or D-shaped. Moreover, the pins 34 could be connected such that they move in unison. For example, the pins 34 could form ends of a single U-shaped pin that moves in a direction into-and-out of the page.

FIGS. 7-18B schematically illustrate one embodiment of a process for mounting the saw blade 6 onto a hub (which houses the blade locking mechanism 30). The surgeon first uses the actuator to depress the locking pins 34 and thereby clear a path for mounting of the saw blade 6 on the hub. Alternatively, the surgeon uses the actuator to release a previous blade after use, and the device remains in this state until a new blade is inserted. The saw blade 6 is then inserted into a slot in the hub of the handpiece (not shown) so that the mounting arm 32 is received in mounting cavity 8. In some embodiments, the insertion direction of the blade can be, but does not have to be, parallel to the longitudinal axis of the blade 6 (i.e., the blade is inserted straight) such that the blade 6 is not angled upon initial insertion into the slot of the hub. The extension arms 10 on the saw blade 6 may have any geometry but in some embodiments (1) the outside leading edges 36 of the extension arms 10 are angled to facilitate insertion of the saw blade 6 into the hub and (2) the inside leading edges 38 are angled to guide the mounting arm 32 into the mounting cavity 8. By way only of example, in one embodiment each inside leading edge 38 is angled so as to be substantially parallel to one of the mounting slots 29a, 29b so that the inside leading edges 38 define approximately the same angle as the mounting slots 29a, 29b. In this embodiment, the outside leading edges 36 are angled relative to each other at an angle approximately twice that of the angle between the inside leading edges 38. Again, however, the geometry of the extension arms 10 may vary from those shown and discussed herein. Once the saw blade 6 is positioned on the mounting arm 32, the surgeon rotates the saw blade 6 and releases the actuator so that the locking pins 34 are free to spring upwardly to engage one of the mounting slots 29a, 29b, gradually biasing the mounting arm 32 into the other of the mounting slots 29a, 29b (the slot of least resistance) until the locking pins 34 can fully extend into their respective positions within mounting slots 29a, 29b to secure the mounting arm 32 in position. Alternatively, the rotary motion of the saw blade automatically releases the actuator and thus the locking pins 34. The locking pins 34 thereby retain the mounting arm 32 in one of the mounting slots 29a, 29b via their engagement with the other of the mounting slots 29a, 29b and in this way prevent the saw blade 6 from backing out of the cam.

If locking pins 34 are provided at the front right and bottom left of the mounting arm 32 (as shown in FIGS. 7-18B), the locking pins 34 will bias and lock the arm in mounting slot 29a. Alternatively, if locking pins 34 are provided at the front left and bottom right of the mounting arm 32 (not shown), the locking pins 34 will bias and lock the mounting arm 34 in mounting slot 29b. It is also contemplated that locking pins 34 may be provided at the front left, front right, bottom left, and bottom right of mounting arm 32 so that the mounting arm 32 can be selectively locked in either of mounting slots 29a, 29b (see FIGS. 19-27). The locking pins 34 may be of any size or shape that enables them to engage the mounting cavity 8 to retain the saw blade 6 and the mounting arm 32 in a substantially fixed position relative to each other. In some embodiments, the locking pins 34 are tapered to facilitate engagement with the mounting cavity 8.

The embodiments disclosed herein create and retain a rigid, secure connection between the saw blade and hub even after repeated and rapid oscillations of the saw blade during use. Indeed, an inherent advantage of the configuration is that the lock is in the direction of travel for the blade (i.e., laterally). Thus, if the blade is not fully secured on the hub (i.e., the mounting arm 32 is not fully engaged in mounting slots 29a or 29b), upon activation and as the blade oscillates laterally, the mounting arm 32 will move further into the mounting slot 29a (or mounting slot 29b) and the locking pins 34 will move further into the mounting slot 29b (or 29a) to thereby secure the mounting arm 32 in the slot 29a, 29b. Moreover, the disclosed connection configuration renders it easy to mount and dismount the saw blade from the hub quickly and without the need for tools. To disconnect the saw blade 6 from the saw, the surgeon simply retracts the locking pins 34 with the actuator and pulls the blade from the saw.

Referring once again to FIG. 18B, the saw blade 6 includes the mounting portion 9 and a planar portion 11. The saw blade has a proximal end 13 and a distal end 17. In the depicted embodiment, the teeth 5 are located on the distal end 17 but other locations are possible. In the depicted embodiment, the planar portion has a narrower width than the proximal and distal ends 13, 15 but other configurations are possible. For example, the saw blade 6 may have a generally uniform width.

Embodiments other than those explicitly disclosed in the figures are also contemplated. For example, the mounting cavity 8 can be formed with a single mounting slot 56 that extends along the blade 6 at an angle to the longitudinal axis of the saw blade 6, as shown in FIG. 41. Apertures 54 shaped to receive locking pins 34 are provided on opposite ends and sides of the slot 56. Saw blades 6 provided with a single mounting slot 56 are mounted on the hub as described above so that pins 34 engage the apertures 54 and thereby bias and lock the blade 6 into the mounting slot 56. The mounting arm 32 need not be rectangular as shown. Rather, any shaped mounting arm 32 may be provided in the cam provided that the mounting cavity 8 on the saw blade is shaped to receive both the mounting arm 32 and the locking pins 34 to ensure a secure connection. For example, the mounting arm 32 could be tapered for ease of insertion or reverse-tapered to enhance blade security. Alternatively, there may be two slots 56 (similar to the embodiment shown in FIG. 7) with diametrically opposed apertures 54 on the ends of one or more slots.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A surgical saw blade for use in orthopaedic surgery, the saw blade comprising:
    a blade body having a proximal end and a distal end, the blade body having a mounting cavity extending distally from the proximal end, the blade body having teeth at the distal end for sawing,
    wherein the blade body has opposing walls that define the mounting cavity, the mounting cavity having a first substantially triangular-shaped opening and a second substantially triangular-shaped opening in communication with, and inverted relative to, the first opening, the first and second openings collectively define two mounting slots that form an angle relative to one another, and
    wherein the opposing walls have first edges extending along two sides of the first substantially triangular-shaped opening and second edges extending along two sides of the second substantially triangular-shaped opening, wherein each of the first edges meets one of the second edges at a corner to define an obtuse angle.

2. The surgical saw blade of claim 1, wherein the first opening and the second opening have rounded corners.

3. The surgical saw blade of claim 1, wherein the first opening includes side walls and a distally-located base wall having curved segments separated by a connecting wall.

4. The surgical saw blade of claim 3, wherein the connecting wall is straight, concave, or convex.

5. The surgical saw blade of claim 1, further comprising a mounting portion and a planar portion extending longitudinally from the mounting portion, and the mounting cavity is located on the mounting portion.

6. The surgical saw blade of claim 5, wherein the planar portion further comprises an offset planar shelf.

7. The surgical saw blade of claim 6, wherein the offset shelf is oriented along the length of the planar portion to allow for longitudinal reciprocation.

8. The surgical saw blade of claim 6, wherein the offset shelf is oriented across the width of the planar portion to allow for lateral reciprocation.

9. The surgical saw blade of claim 5, wherein the planar portion further comprises teeth.

10. The surgical saw blade of claim 9, wherein the teeth are arranged in a linear or arcuate fashion.

11. The surgical saw blade of claim 9, wherein the teeth are oriented along the length of the planar portion to allow for longitudinal reciprocation.

12. The surgical saw blade of claim 9, wherein teeth are oriented across the width of the planar portion to allow for lateral reciprocation.

13. A surgical saw blade for use in orthopaedic surgery, the saw blade comprising:
  a blade body having a proximal end and a distal end, the blade body having a mounting cavity extending distally from the proximal end, the blade body having teeth at the distal end for sawing,
  wherein the mounting cavity is defined between opposing walls of the blade body, the opposing walls having:
    a pair of spaced leading edges that define a proximal entry to the mounting cavity;
    a pair of first curved segments that each extend distally from a respective one of the leading edges, the first curved segments having a width therebetween that increases in a distal direction along portions of the curved segments;
    a pair of first linear segments that each extend distally from a respective one of the curved segments to an apex, the first linear segments having a width therebetween that decreases in a distal direction along the first linear segments; and
    a pair of second linear segments that each extend distally from a respective one of the apexes, the second linear segments having a width therebetween that increases in a distal direction along the second linear segments.

14. The surgical saw blade of claim 13, wherein the blade body has a base wall defining a distal boundary of the mounting cavity, the base wall comprising:
  a pair of second curved segments that each extend from a respective one of the second linear segments; and
  a connecting wall that joins the second curved segments.

15. The surgical saw blade of claim 13, wherein each of the first linear segments is parallel the second linear segment of the opposite wall.

16. The surgical saw blade of claim 13, wherein the curved segments are located distal to the leading edges.

17. A surgical saw blade for use in orthopaedic surgery, the saw blade comprising:
  a blade body having a proximal end and a distal end, the blade body having a mounting cavity extending distally from the proximal end, the blade body having teeth for sawing located distal to the mounting cavity,
  wherein the blade body has opposing walls that define the mounting cavity, each of the opposing walls having a proximal linear edge that meets a corresponding distal linear edge at a corner, and each of the proximal linear edges is oriented at an obtuse angle with respect to the corresponding distal linear edge.

18. The surgical saw blade of claim 17, wherein the proximal linear edges have a width therebetween that decreases in a distal direction along the first linear segments; and
  wherein the distal linear segments have a width therebetween that increases in a distal direction along the second linear segments.

* * * * *

UNITED STATES PATENT AND TRADEMARK OFFICE
CERTIFICATE OF CORRECTION

Page 1 of 1

PATENT NO. : 8,734,450 B2
APPLICATION NO. : 13/210017
DATED : May 27, 2014
INVENTOR(S) : Ryan Lloyd Landon It is certified that error appears in the above-identified patent and that said Letters Patent is hereby corrected as shown below:

On the title page, item (73) Assignee, replace "TX" with --TN--.

Signed and Sealed this
Eighteenth Day of November, 2014

Michelle K. Lee
*Deputy Director of the United States Patent and Trademark Office*